(12) United States Patent
Wu et al.

(10) Patent No.: US 10,501,758 B2
(45) Date of Patent: *Dec. 10, 2019

(54) RECOMBINANT BACULOVIRUS AND METHOD FOR USING THE SAME FOR PREPARING RECOMBINANT ADENO-ASSOCIATED VIRUS VECTOR

(71) Applicant: WUHAN INSTITUTE OF PHYSICS AND MATHEMATICS, CHINESE ACADEMY OF SCIENCES, Wuhan (CN)

(72) Inventors: Yang Wu, Wuhan (CN); Fuqiang Xu, Wuhan (CN); Xiaobin He, Wuhan (CN)

(73) Assignee: WUHAN INSTITUTE OF PHYSICS AND MATHEMATICS, CHINESE ACADEMY OF SCIENCES, Wuhan (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/884,470

(22) Filed: Jan. 31, 2018

(65) Prior Publication Data

US 2018/0155740 A1 Jun. 7, 2018

Related U.S. Application Data

(63) Continuation-in-part of application No. PCT/CN2015/095751, filed on Nov. 27, 2015.

(30) Foreign Application Priority Data

Sep. 23, 2015 (CN) .......................... 2015 1 0612946

(51) Int. Cl.
*C12N 7/00* (2006.01)
*C12N 15/86* (2006.01)
*A61K 48/00* (2006.01)

(52) U.S. Cl.
CPC ............ *C12N 15/86* (2013.01); *A61K 48/005* (2013.01); *C12N 7/00* (2013.01);
(Continued)

(58) Field of Classification Search
None
See application file for complete search history.

(56) References Cited

U.S. PATENT DOCUMENTS

| 8,679,837 B2 | 3/2014 | Zolotukhin et al. |
| 2003/0148506 A1 | 8/2003 | Kotin et al. |
| 2005/0069929 A1* | 3/2005 | Chestnut ................ C12N 15/10 435/6.12 |

FOREIGN PATENT DOCUMENTS

| WO | WO-2011140279 A1 * | 11/2011 | ........... A61K 48/005 |

OTHER PUBLICATIONS

M. Kozak, Initiation of translation in prokaryotes and eukaryotes, Gene, Jul. 1999, pp. 187-208, vol. 234, issue 2, Elsevier, Netherlands.

(Continued)

*Primary Examiner* — M Franco G Salvoza
(74) *Attorney, Agent, or Firm* — Matthias Scholl P.C.; Matthias Scholl

(57) ABSTRACT

A recombinant baculovirus, including: an adeno-associated virus Rep gene, an adeno-associated virus Cap gene, and an recombinant adeno-associated virus genome ITR-GOI (gene of interest) flanked by rAAV inverted terminal repeats (ITR). The ITR-GOI includes a 5' terminal nucleic acid fragment and a 3' terminal nucleic acid fragment. The ITR-GOI is linked to an expression cassette of the Cap gene and an expression cassette of the Rep gene through the 5' terminal nucleic acid fragment and the 3' terminal nucleic acid fragment, respectively.

12 Claims, 13 Drawing Sheets

Specification includes a Sequence Listing.

(52) U.S. Cl.
CPC .............. *C12N 2710/14044* (2013.01); *C12N 2710/14143* (2013.01); *C12N 2710/14144* (2013.01); *C12N 2750/14143* (2013.01); *C12N 2750/14152* (2013.01); *C12N 2800/22* (2013.01)

(56) References Cited

OTHER PUBLICATIONS

Y. Chen, Production of adeno-associated virus mediated by Bac-to-Bac baculovirus insect expression system, Medicine and Health Sciences of Chinese Master's Theses Full-text Database, 2012, pp. E072-733, No. 10, China Academic Journal (CD) Electronic Journals Publishing House Co., Ltd., China.

V.A. Luckow et al., Efficient generation of infectious recombinant baculoviruses by site-specific transposon-mediated insertion of foreign genes into a baculovirus genome propagated in *Escherichia coli*, Journal of Virology, 1993, pp. 4566-4579, vol. 67, No. 8, American Society for Microbiology, United States.

M. Urabe et al., Insect cells as a factory to produce adeno-associated virus type 2 vectors, Human Gene Therapy, Nov. 1, 2002, pp. 1935-1943, vol. 13, No. 16, Mary Ann Liebert, Inc., United States.

E. Kohlbrenner EL AL., Successful production of pseudotyped rAAV vectors using a modified baculovirus expression system, Molecular Therapy, Dec. 2005, pp. 1217-1225, vol. 12, No. 6, The American Society of Gene Therapy, United States.

H. Chen, Intron splicing-mediated expression of AAV Rep and Cap genes and production of AAV vectors in insect cells, Molecular Therapy, May 2008, pp. 924-930, vol. 16, No. 5, The American Society of Gene Therapy, United States.

R.H. Smith et al., A simplified baculovirus-AAV expression vector system coupled with one-step affinity purification yields high-titer rAAV stocks from insect cells, Molecular Therapy, Nov. 2009, pp. 1888-1896, vol. 17, No. 11, The American Society of Gene & Cell Therapy, United States.

G. Aslanidi et al., An inducible system for highly efficient production of recombinant adeno-associated virus (rAAV) vectors in insect Sf9 cells, Proceedings of the National Academy of Sciences of the United States of America, Mar. 31, 2009, pp. 5059-5064, vol. 106, No. 13, United States National Academy of Sciences, United States.

M. Mietzsch et al., OneBac: platform for scalable and high-titer production of adeno-associated virus serotype 1-12 vectors for gene therapy, Human Gene Therapy, Mar. 2014, pp. 212-222, vol. 25, No. 3, Mary Ann Liebert, Inc., United States.

M. Mietzsch et al., OneBac 2.0: Sf9 cell lines for production of AAV1, AAV2, and AAV8 vectors with minimal encapsidation of foreign DNA, Human Gene Therapy Methods, 2017, pp. 15-22, vol. 28, No. 1, Mary Ann Liebert, Inc., United States.

Y. Wu et al., A recombinant baculovirus efficiently generates recombinant adeno-associated virus vectors in cultured insect cells and larvae, Molecular Therapy Methods & Clinical Development, Sep. 2018, pp. 38-47, vol. 10, The American Society of Gene & Cell Therapy, United States.

\* cited by examiner

RECOMBINANT BACULOVIRUS AND METHOD FOR USING THE SAME FOR PREPARING RECOMBINANT ADENO-ASSOCIATED VIRUS VECTOR

CROSS-REFERENCE TO RELATED APPLICATIONS

This application is a continuation-in-part of International Patent Application No. PCT/CN2015/095751 with an international filing date of Nov. 27, 2015, designating the United States, now pending, and further claims foreign priority benefits to Chinese Patent Application No. 201510612946.8 filed Sep. 23, 2015. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The disclosure relates to gene therapy, and more particularly relates to a recombinant baculovirus and a method of using the same for producing a recombinant adeno-associated virus vector.

Description of the Related Art

At present, there are two main methods for producing recombinant adeno-associated virus (rAAV) on a large scale by the baculovirus expression system: Two-Bac system and One-Bac system based on a packaging cell line. In Two-Bac system, one baculovirus genome integrates the AAV Rep and Cap genes, and another baculovirus genome integrates the rAAV genome ITR-GOI (gene of interest flanked by AAV inverted terminal repeats). The two recombined baculoviruses were used to co-infect host cells to produce rAAV. In One-Bac system that depends on a packaging cell line, the packaging cell line Sf9/Rep-Cap integrated both the Rep and Cap gene inducible expression cassettes. The Rep gene or Cap gene is under the control of the regulated sequences including baculovirus hr2 enhancer sequence and the AAV Rep protein binding sequence (RBE) and baculovirus late polyhedron (PH) promoter. The packaging cell line expresses Rep and Cap genes to produce rAAV after being infected with a recombinant baculovirus that contains the rAAV genome ITR-GOI.

However, in the Two-Bac system, the yield of rAAV is low because the two baculoviruses co-infect the cells at a low efficiency and cannot fully utilize the capacity of each cell. The two baculoviruses infection is a randomized process which is difficult to be optimized, leading to unstable rAAV quality in different production batches. In the One-Bac system based on the Sf9/Rep-Cap packaging cell line, it is difficult to obtain high efficiency packaging cell line integrated both Rep gene and Cap genes, and it is not versatile to establish different kinds of cell lines carrying different Cap genes for the production of different serotypes of rAAV. Thus, the One-Bac method has low flexibility and versatility, and thus, is not very widely used.

SUMMARY OF THE INVENTION

In view of the above-described problems, it is an objective of the invention to provide a recombinant baculovirus and application of the same. One objective of the invention is to transform the AAV Rep gene, the Cap gene, and the rAAVgenome ITR-GOI into single baculovirus genome to form an expression carrier of rAAV, thereby resolving the problems of low flexibility, low versatility, high complexity, low virus yield, unstable virus quality, and high cost of the existing methods for large-scale production of rAAV.

To achieve the above objective, according to one aspect of the invention, there is provided a recombinant baculovirus that comprises a Rep gene, a Cap gene, and a rAAVgenome ITR-GOI, and the ITR-GOI is linked to an expression cassette of the Cap gene and an expression cassette of the Rep gene through the 5' terminal nucleic acid fragment and the 3' terminal nucleic acid fragment, respectively.

In a class of this embodiment, the Rep gene has a sequence which is a codon-optimized sequence based on ribosomal leaky scanning principle, and preferably has a sequence represented by SEQ ID No. 1, SEQ ID No. 2, or SEQ ID No. 3.

In a class of this embodiment, the Cap gene has a sequence which is a codon-optimized sequence based on the ribosomal leaky scanning principle and preferably has a sequence represented by SEQ ID No. 4, SEQ ID No. 5, or SEQ ID No. 6.

In a class of this embodiment, each of two ends of the ITR-GOI comprises an AAV inverted terminal repeat (ITR); and a gene of interest (GOI) is disposed between the two ends of the ITR core expression cassette. The ITR preferably has a sequence represented by SEQ ID No. 7.

In a class of this embodiment, the 5' terminal nucleic acid fragment or the 3' terminal nucleic acid fragment is a ligation nucleic acid fragment of 80-140 bp, and preferably has a sequence represented by SEQ ID No.8 or SEQ ID No. 9.

In a class of this embodiment, the adeno-associated virus is adeno-associated virus type 2.

According to another aspect of the invention, there is provided a method for producing recombinant adeno-associated virus vector, which is a viral vector for gene therapy.

In a class of this embodiment, the method comprises:
(1) constructing a recombinant baculovirus by integrating AAV Rep gene, Cap gene, and rAAV genome ITR-GOI contained a functional gene into the genome of the recombinant baculovirus;
(2) infecting host cells with the recombinant baculovirus prepared in the step (1) to produce a large amount of recombinant adeno-associated virus; and
(3) purifying the recombinant adeno-associated virus produced in step (2).

In a class of this embodiment, in (1), a pFast. Bac. Dual shuttle vector based on Bac to Bac system is used.

Advantages of the recombinant baculovirus and the application thereof according to embodiments of the disclosure are summarized as follows:

Through method modification and optimization, the disclosure utilizes a baculovirus to provide essential packaging elements for rAAV production, i.e., the Rep gene, the Cap gene, and the rAAV genome ITR-GOI, with biological functions and compatibility of the ITR-GOI with the other two genes. In the invention, rAAV can be produced by single recombinant baculovirus infection upon host cells, with a high percentage of intact rAAV particles and high virus quality. Moreover, the rAAV production capacity of each cell is obviously increased. The invention has high flexibility, high versatility, high virus quality, and high virus yield and, therefore, is suitable for large-scale production and can effectively solve the problem of large-scale preparation of rAAV.

DETAILED DESCRIPTION OF THE EMBODIMENTS

To make the objectives, technical solutions, and advantages of the invention more comprehensible, the disclosure is further described in detail below with reference to the accompanying drawings and embodiments. It should be understood that the specific embodiments described herein are merely used to explain the invention, and are not intended to limit the invention. In addition, the technical features involved in the various embodiments of invention described below can be combined with each other as long as the two do not conflict with each other.

Figure 1:
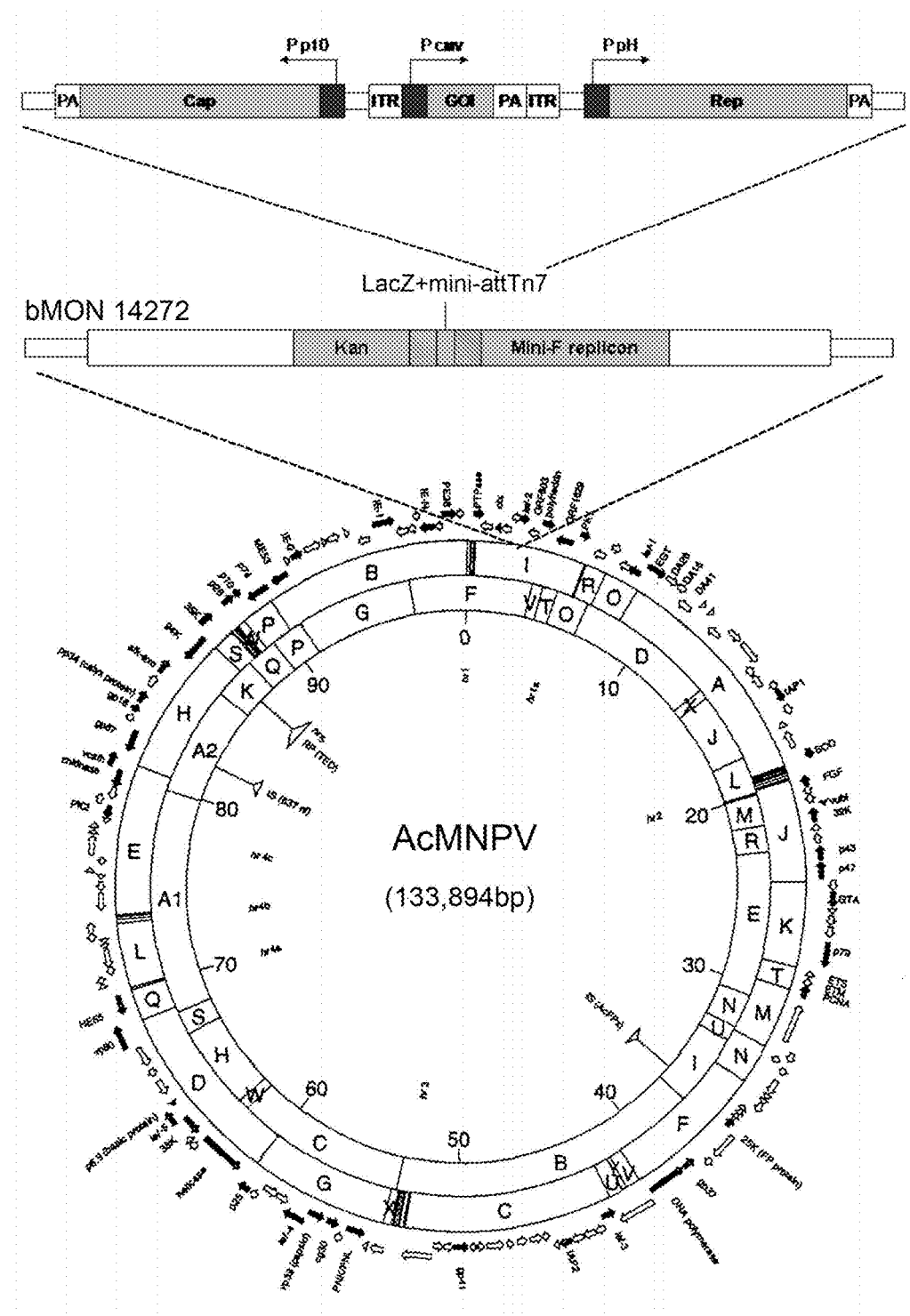
FIG. 1 is a schematic diagram of a recombinant baculovirus.

The recombinant baculovirus of the invention has a genome as shown in FIG. 1, which is preferably AcMNPV clone E2 (genome sequence of Genbank accession No. KM667940.1, see, Journal of Virology, August 1993, p. 4566-4579) or AcMNPV clone C6 (genome sequence of Genbank accession No. NC_001623.1) integrated with the Rep gene, the Cap gene, and rAAV genome ITR-GOI. The baculovirus AcMNPV is double-stranded circular DNA of 133,894 bp. The sequence and mapping references is described in Virology, 1994. 202 (2): p. 586-605, and the structure of AcMNPV Bacmid (bMON14272) is described in J Virol, 1993. 67 (8): p. 4566-79. The Rep gene, the Cap gene, and the ITR-GOI were inserted into the Tn7 site of bacmid (bMON14272). The Rep gene and the Cap gene are optimized based on ribosomal leaky scanning principle. The rAAV genome ITR-GOI comprises a pair inverted terminal repeats (ITR) of AAV genome at two ends and a gene of interest (GOI) in the middle, and is linked to an expression cassette of the Rep gene and the Cap gene through a 5' terminal nucleic acid fragment or a 3' terminal nucleic acid fragment. The Rep gene and the Cap gene can be upstream or downstream of the ITR core expression cassette.

The Rep gene is codon-optimized based on ribosomal leaky scanning principle, and can be transcribed into an mRNA by the PH promoter to achieve the functional expression of the Rep72 and Rep52. The sequence of Rep gene is one of SEQ ID Nos. 1 to 3.

The Cap gene is codon-optimized based on ribosomal leaky scanning principle, and can be transcribed into an mRNA through the P10 promoter to achieve functional expression of the three capsid proteins of VP1, VP2, and VP3 near the natural ratio (1:1:10). The sequence of the Cap gene is one of SEQ ID Nos. 4 to 6.

The ITR-GOI is linked to the expression cassette of the Rep gene and the Cap gene by the ligation nucleic acid fragments at both ends. ITR is a terminal inverted repeat of the AAV genome, preferably the ITR sequence of AAV type 2 as SEQ ID No. 7. The 5' or 3' terminal nucleic acid fragment is preferably a ligation nucleic acid sequence of between 80 bp-140 bp, represented by SEQ ID No. 8 or SEQ ID No. 9. The ITR-GOI core expression cassette is a GFP gene expression cassette containing a CMV promoter, a GFP gene, and a ploy A (PA) component.

Figure 2A:
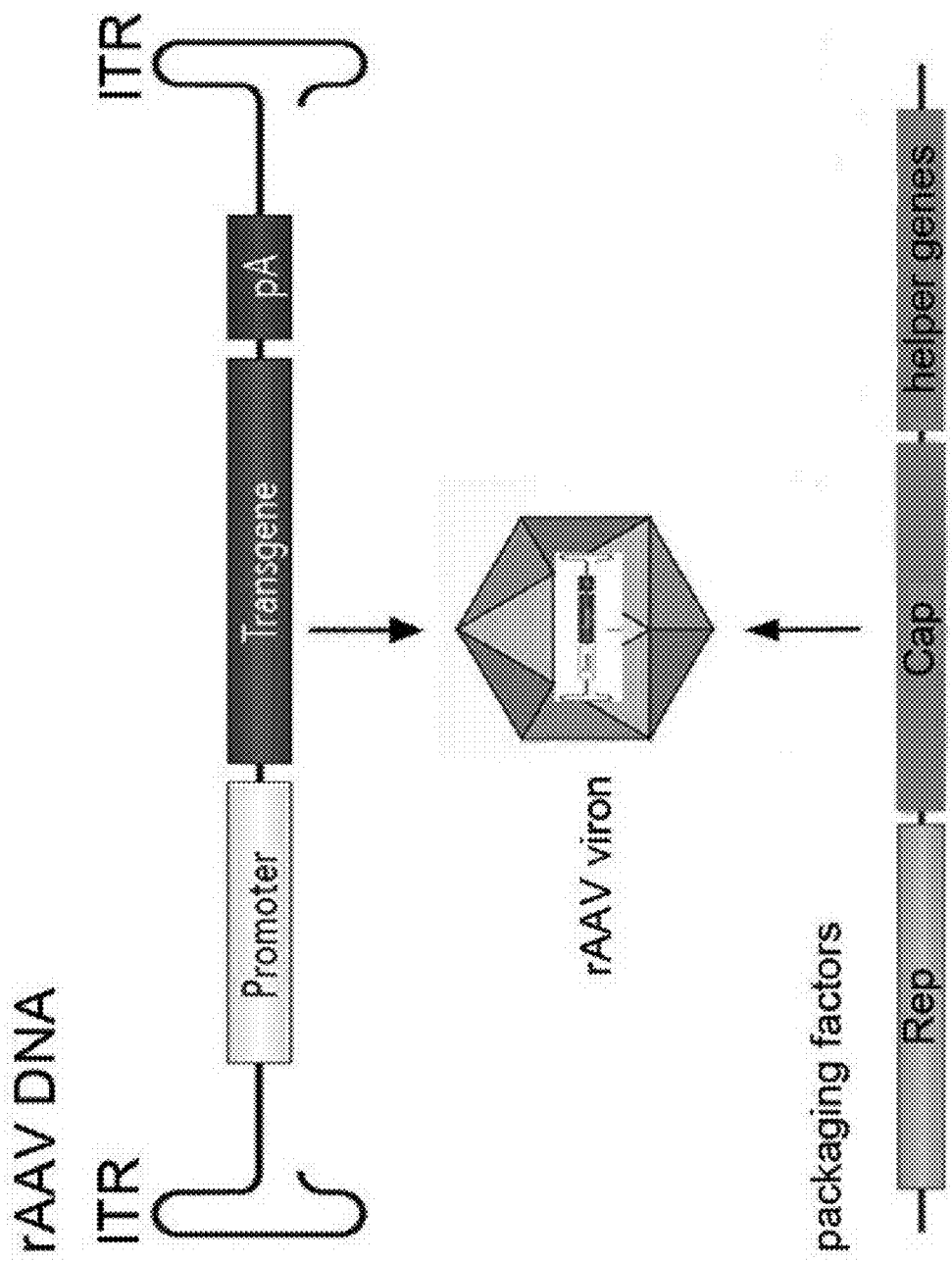
FIG. 2A is a schematic diagram of a packing process of a rAAV.
Figure 2B:
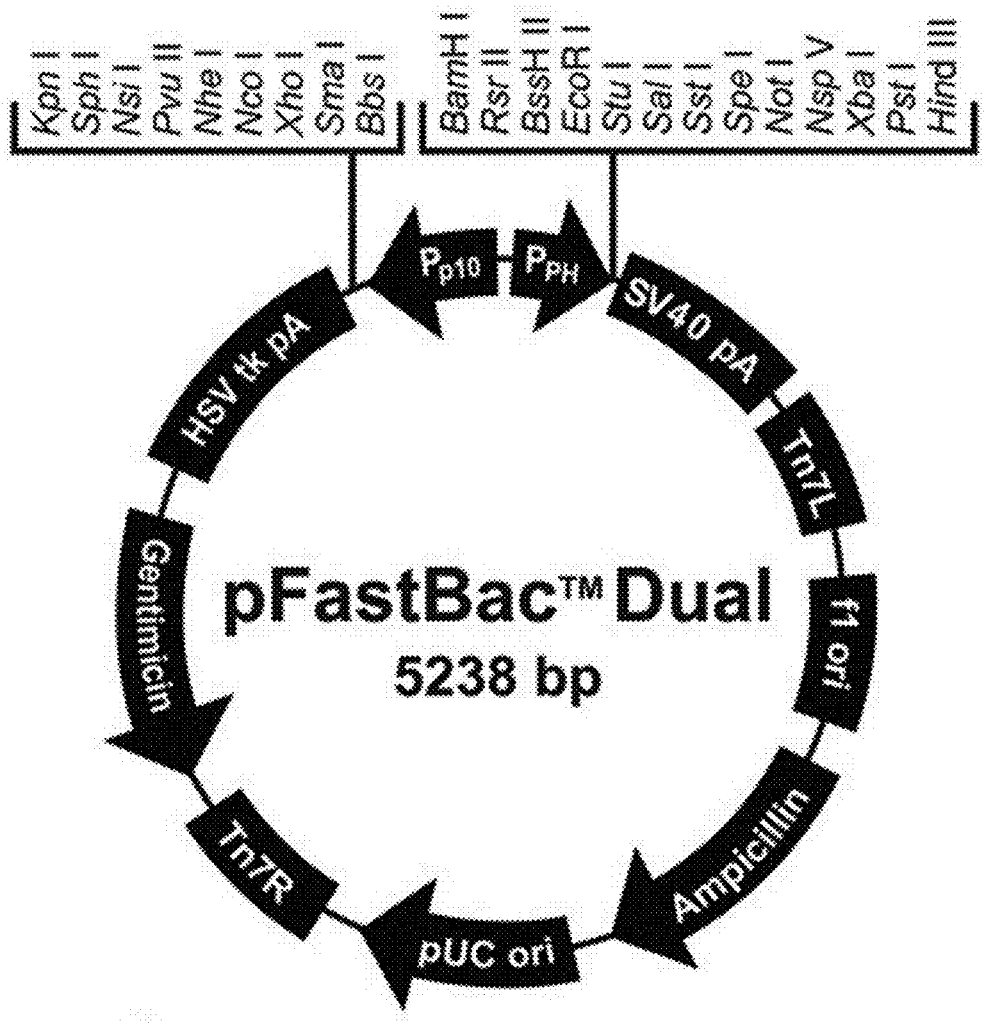
FIG. 2B is a schematic diagram of a shuttle plasmid pFast. Bac. Dual (pFBD) of the baculovirus expression system.
Figure 2C:
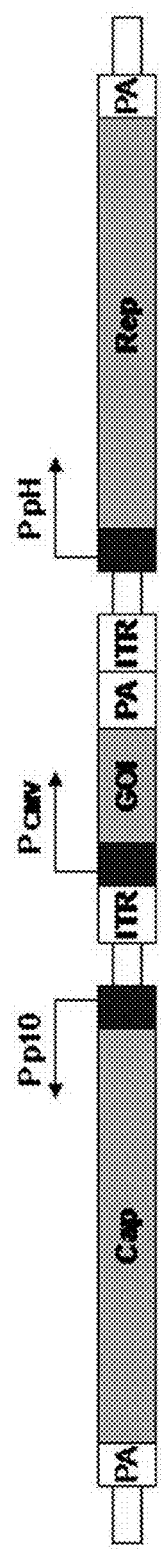
FIG. 2C is a schematic diagram of the structure of a recombinant shuttle plasmid integrated with the components required for producing rAAV.

The preferred combination of the Rep, the Cap, and the ITR-GOI integrated into the baculovirus genome is shown in FIG. 2C.

The recombinant baculovirus of the invention is prepared as follows:

A. The codon-optimized Rep and Cap genes are obtained by gene synthetic methods; The ITR-GOI is obtained by conventional molecular cloning techniques; and B. The Rep gene, the Cap gene, and the ITR-GOI obtained in step A are integrated by molecular cloning into pFast. Bac. Dual (pFBD) shuttle vector according to the Bac to Bac system to obtain the recombinant baculovirus.

The genomic DNA of rAAV vector contains exogenous gene of interest which replaces the AAV coding gene and the ITR sequences which is required for virus replication and packaging. The Rep gene and the Cap gene and helper virus functions were supplied by trans-compensation for the production of rAAV, as shown in FIG. 2A. It is very difficult to integrate the Rep gene, the Cap gene, and ITR-GOI into single baculovirus. First, the cloning combination and operation of the three elements are complicated and difficult. Second, each of the three elements has a key role in the successful production of rAAV, and the combination of the three elements cannot disrupt the function of each other. Therefore, in traditional methods, the three elements are either separately integrated into host cells or baculoviruses. The invention optimized the sequences of the Rep gene and the Cap gene and constructed the ligation sequences at the two ends of the ITR-GOI so as to integrate the Rep gene, the Cap gene, and the ITR-GOI into pFBD shuttle vector and maintain the biological function of the three elements, thereby achieving large-scale production of rAAV of stable quality. As such, by replacing the exogenous gene of interest (GOI) fragment carried by the ITR-GOI or replacing the Cap gene or Rep gene of AAV of different serotype, rAAV can be flexibly produced to meet the requirement.

Figure 2D:
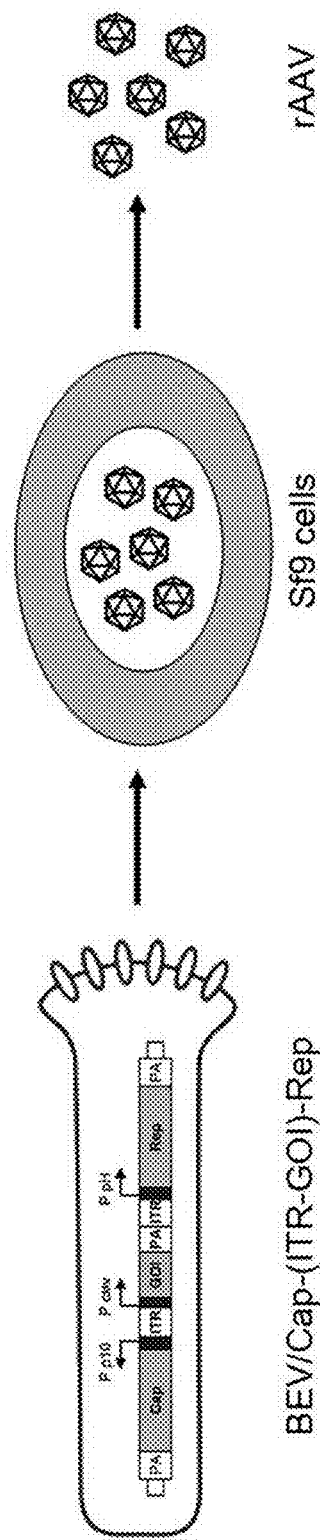
FIG. 2D is a schematic diagram of the process for producing rAAV by infecting Sf9 cells with the recombinant baculovirus.

The recombinant baculovirus of the invention for producing the recombinant adeno-associated virus vector for gene therapy is prepared as follows:

(1) constructing a recombinant baculovirus by integrating AAV Rep gene, Cap gene, and rAAV genome ITR-GOI contained a functional gene in the genome of the recombinant baculovirus;

Preferably, the recombinant baculovirus of the invention uses the pFast. Bac. Dual (pFBD) shuttle vector as a backbone carrier (as shown in FIG. 2B) and contains three optimized functional components (as shown in FIG. 2C), and takes advantage of the Bac to Bac system;

(2) infecting a host cell with the recombinant baculovirus prepared in the step (1) to produce a large amount of recombinant adeno-associated virus; Specifically, the following steps are performed: infecting Sf9 insect cells with the recombinant baculovirus (BEV) (as shown in FIG. 2D); suspension cultured Sf9 cells in shake flasks to a cell density of $3 \times 10^6$ cells/ml; infecting the Sf9 cells with recombinant baculovirus (BEV) at a multiplicity of infection (MOI) of 5, shaking culturing the infected cells at 27° C., 120 rpm for 3 days; centrifuging cell suspension at 3000 rpm for 5 minutes, and collecting culture supernatant and cell pellet; and (3) purifying the recombinant adeno-associated virus prepared in step (2).

rAAV is mainly present in cell pellets. The rAAV produced can be used for further application after separation and purification operations.

The Bac-A system of the invention utilizes a recombinant baculovirus to provide the replication, packaging elements for rAAV production and the ITR-GOI, resulting in a higher percentage of intact rAAV particles and high virus quality. Moreover, the rAAV production capacity of a single cell has also been obviously improved. The Bac-A system has high flexibility, high versatility, high virus quality, and high yield, which is suitable for large-scale production and can effectively solve the problem of large-scale preparation of rAAV.

The disclosure is applicable to various types of adeno-associated virus. The following examples are based on adeno-associated virus type 2 (AAV2):

Example 1: Preparation and Amplification of Recombinant Baculovirus (BEV)

The pFast. Bac. Dual (pFBD) shuttle vector in Bac to Bac baculovirus expression system was used for integrating the three major components required for the preparation of rAAV, i.e., the Cap gene, the Rep gene, the ITR-GOI, in a recombinant baculovirus. In the example, the Rep gene based on AAV type 2 has a sequence which is a codon-optimized sequence based on ribosomal leaky scanning principle, and the Rep gene was under the control of PH promoter to achieve the functional expression of Rep72 and Rep52. The Rep gene sequence is represented SEQ ID No. 1, SEQ ID No. 2, or SEQ ID No. 3 (corresponding to RepA, RepB, and RepC, respectively). In the example, the Cap gene based on AAV type 2 was codon-optimized based on the ribosomal leaky scanning principle. The Cap gene was under the control of the P10 promoter to achieve expression of the capsid proteins of VP1, VP2, and VP3 near natural ratio (1:1:10). The Cap gene sequence is SEQ ID No. 4, SEQ ID No. 5, or SEQ ID No. 6 (corresponding to CapA, CapB, and CapC, respectively). The ITR use the ITR nucleic acid sequence of AAV type 2, i.e., the sequence of SEQ ID No. 7. The ITR-GOI contains expression cassette of green fluorescent protein (GFP), the expression of which is controlled by CMV promoter so as to detect rAAV activity. The ITR-GOI is linked to the expression cassettes of the Rep gene and the Cap gene via a 5' terminal nucleic acid fragment or a 3' terminal nucleic acid fragment. The 5' terminal nucleic acid fragment or the 3' terminal nucleic acid fragment is a sequence of SEQ ID No. 4 (link A) or SEQ ID No. 5 (link B).

In the example, three representative combinations of the major components of the recombinant baculovirus were selected;

1. CapA-LinkA-(ITR-GFP)-linkA-RepA
2. CapB-LinkB-(ITR-GFP)-linkB-RepB
3. CapC-LinkA-(ITR-GFP)-linkB-RepC A recombinant shuttle plasmid pFBD/Cap-(ITR-GFP)-Rep was constructed by placing the ITR-GFP between the P10 and PH promoters of the pFBD vector by ligating the nucleic acid fragments according to the conventional molecular cloning technique as shown in FIG. 2C.

The sequence of P10 promoter is:

(SEQ ID No. 10)
ATACGGACCTTTAATTCAACCCAACACAATATATTATAGTTAAATAA

GAATTATTATCAAATCATTTGTATATTAATTAAAATACTATACTGTA

AATTACATTTTATTTACAATCACTCGAC

The sequence of PH promoter is:

(SEQ ID No. 11)
ATCATGGAGATAATTAAAATGATAACCATCTCGCAAATAAATAAGTA

TTTTACTGTTTTCGTAACAGTTTTGTAATAAAAAAACCTATAAATAT

TCCGGATTATTCATACCGTCCCACCATCGGGCGC

The sequence between P10 promoter and PH promoter is (SEQ ID No. 12)
ACTCCGGAATATTAATAG The recombinant shuttle plasmid was transformed into DH10Bac containing the AcMNPV baculovirus genome according to the Bac-to-Bac system protocol. Recombinant baculovirus genome (Bacmid) was obtained by Tn7 transposon element-mediated recombination. Positive bacteria containing recombinant Bacmid were obtained by blue-white screening and PCR identification. Recombinant Bacmid was extracted and purified and transfected into adherently cultured Sf9 cells. Sf9 cells were completely infected with recombinant baculovirus and showed obvious cytopathic effect (CPE). The cell culture was centrifuged at 3000 rpm for 5 min, and the resulting recombinant baculovirus was present in the supernatant.

Figure 3A:
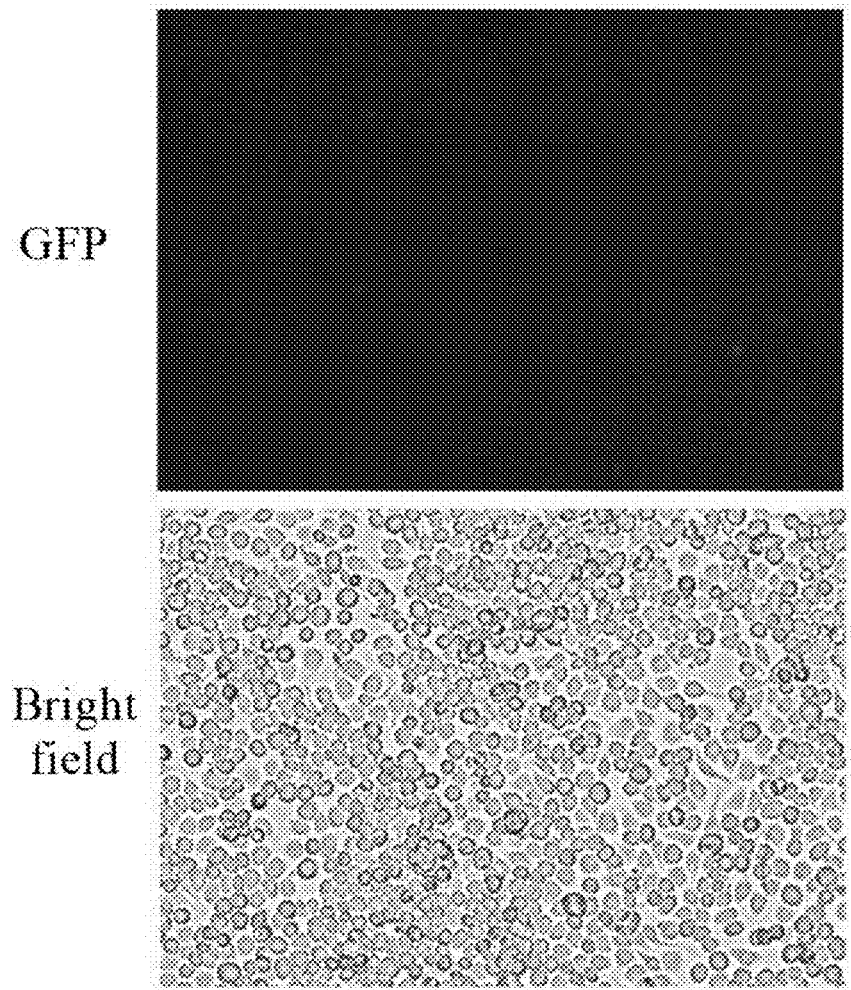
FIG. 3A is a schematic diagram of fluorescence microscopy images of a control group of the Sf9 cell.
Figure 3B:
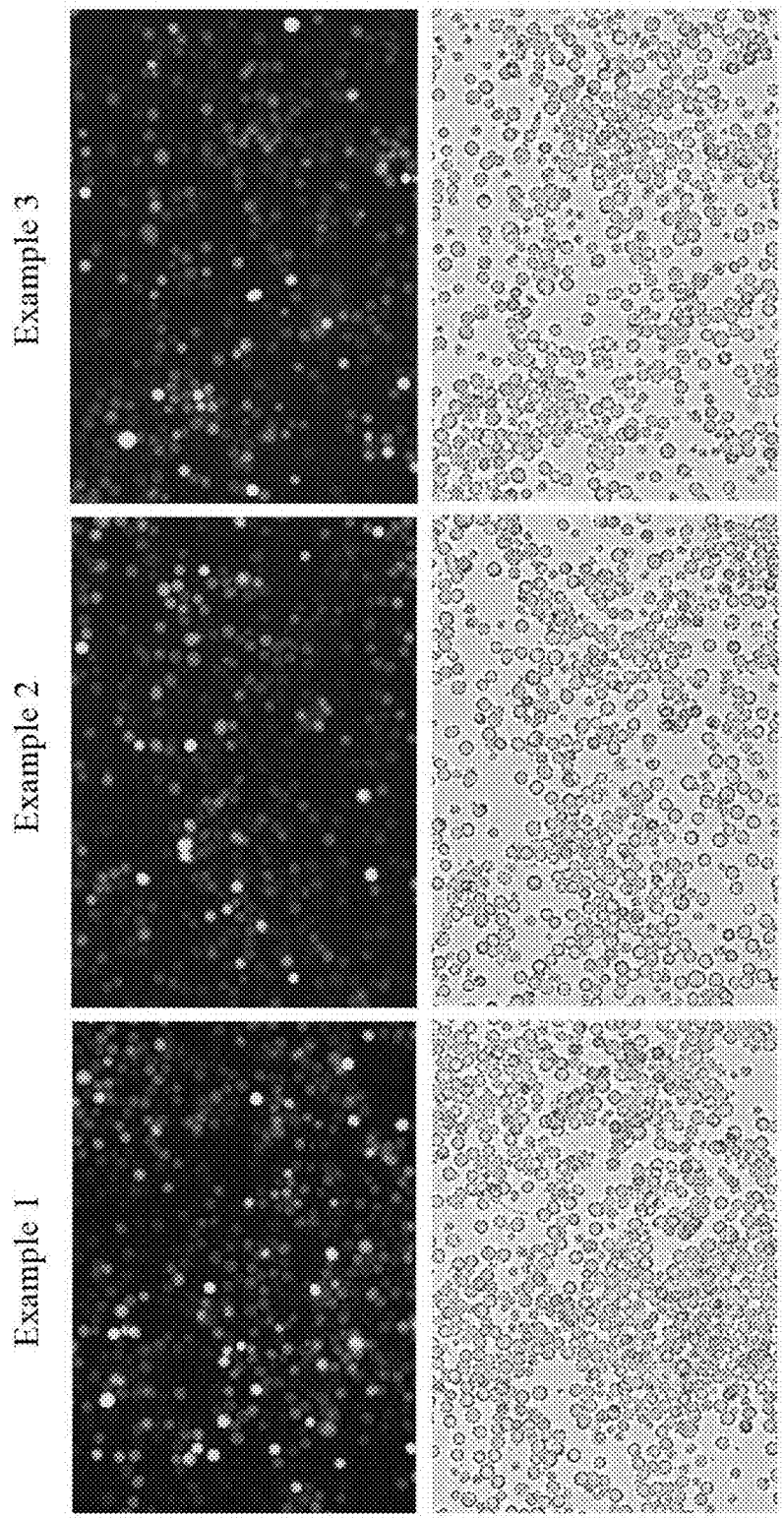
FIG. 3B is fluorescence microscopy images of the experimental group three days after infecting Sf9 cells with the recombinant baculovirus in Examples 1-3.

The supernatant was used to infect adherently cultured Sf9 cells and cultured for 3 days. The control group of uninfected Sf9 cells were in the normal state without GFP expression (as shown in FIG. 3A), while the Sf9 cells infected by the BEV of combinations 1, 2, and 3 had a significant CPE phenomenon and obvious GFP expression, as the results shown in FIG. 3B, showing that the combinations successfully produced recombinant baculovirus. BEV produced from transfected Sf9 cells was used to infect adherently cultured or suspension cultured Sf9 cells, and the infected Sf9 cells showed CPE after 3 days; then the cell culture fluid was centrifuged at 3000 rpm for 5 min, and the BEV supernatant was obtained. The titer of the BEV was determined by the method of Fluorescent Quantitative PCR. See, Proc Natl Acad Sci USA, 2009. 106 (13): 5059-64.

Example 2: Production of rAAV Via Infecting the Sf9 Cell Line with BEV and Verification of Virus Activity Thereof The Sf9 cells cultured in suspension were infected with BEV prepared in Example 1 at MOI=5. Three days after infection, the cell culture was centrifuged at 3000 rpm for 5 minutes to collect the culture supernatant and the cell pellet. The BEV was released mainly into the supernatant of the medium by secretion, and some of the un-released BEV was also present in Sf9 cells. The rAAV was mainly present in the nuclei of Sf9 cells, and some of the rAAV was released into the supernatant because of the cytopathic effect (CPE) after infection of Sf9 cells. As a result, BEV and rAAV were present in both culture supernatants and cell pellets.

Figure 4A:
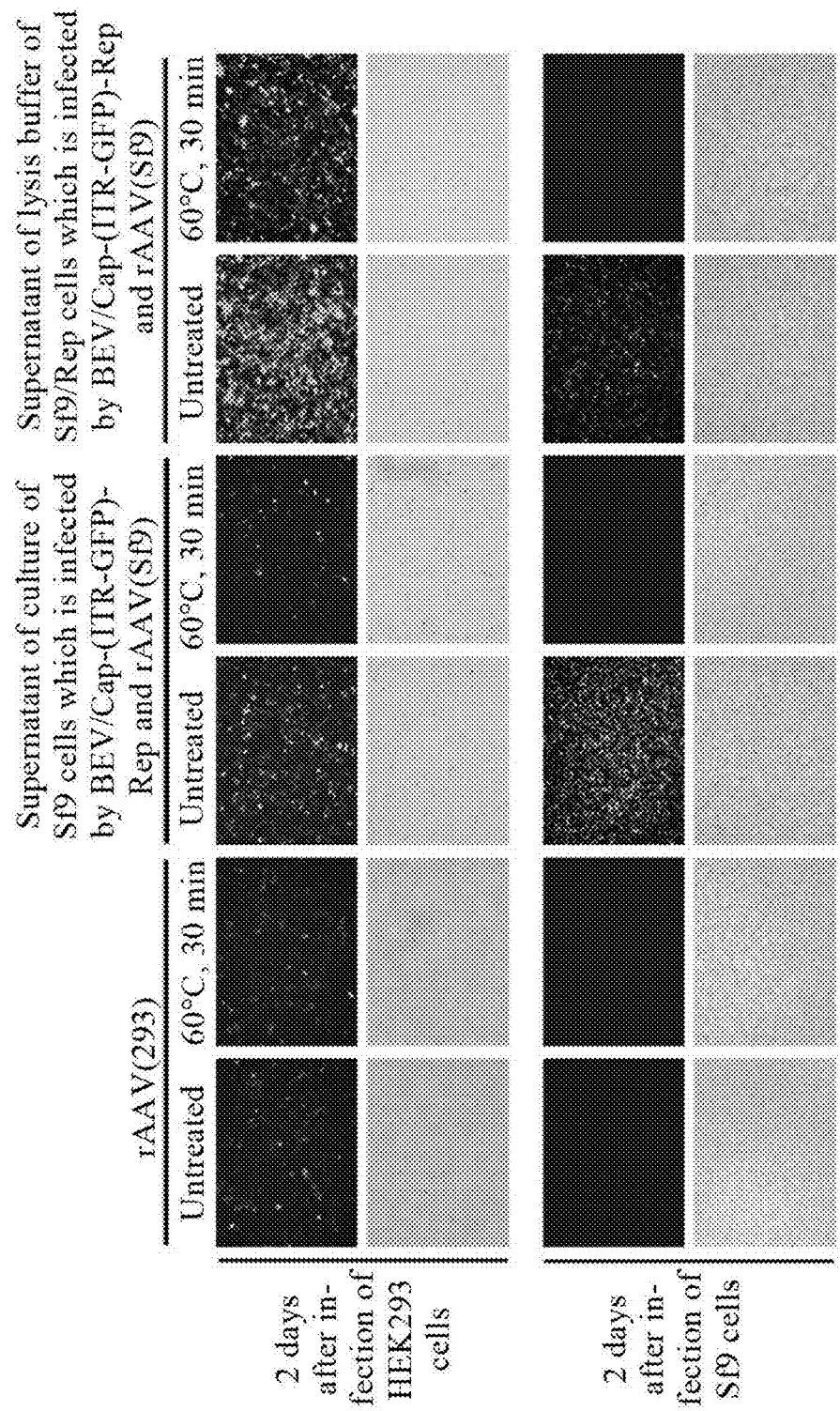
FIG. 4A is a verification result of rAAV prepared according to combination 1 in infecting HEK293 cells and Sf9 cells.

The activity of the rAAV produced by Sf9 cells infected with the recombinant baculovirus was tested. For the combination 1 of Example 1, the experimental results of virus infection of HEK293 cells and Sf9 cells confirmed that the Bac-A system produced rAAV. The experimental results are shown in FIG. 4A. The detailed process and the results are as follows: The cell pellets were lysed by freeze-thaw using liquid nitrogen and a 37° C. water bath for three times, then centrifuged at 5000 rpm for 5 min and supernatant of cell lysis was collected. Because rAAV was enveloped, its activity was not affected by heating at 60° C. for 30 minutes, whereas recombinant baculovirus (BEV) was enveloped and lost its activity after treatment at 60° C. for 30 minutes. A simple infection-based method was used to test the rAAV activity (FIG. 4.A). For rAAV2 (293 cells derived) samples, in 293 cells-based infection assays, both the treated and untreated can express GFP. In Sf9 cells-based infection assays, both the treated and untreated cannot express GFP, it indicates that rAAV2 do not infect Sf9 cells. For BEV/Cap-(ITR-GFP)-Rep supernatant samples, which contain the major secreted BEV and some rAAV. In 293 cells-based infection assays, both the treated and untreated can express GFP, while the GFP expression of the treated decrease significantly, because inactive BEV do not express GFP and only some rAAV can express GFP. In Sf9 cells-based infection assays, the untreated can express GFP, but the treated cannot express GFP. For BEV/Cap-(ITR-GFP)-Rep infected Sf9 cells lysate supernatant samples, which contain some non-secret BEVs and the major rAAV. In 293 cells-based infection assays, both the treated and untreated can express GFP, but GFP expression of the treated decrease slightly. It indicates that there is large amount of rAAVs expressing GFP. In Sf9 cells-based infection assays, the untreated can express GFP, while the treated cannot express GFP (FIG. 4A). The results demonstrate that rAAV2 is successfully generated in the novel BEV infected Sf9 cells.

Figure 4B:
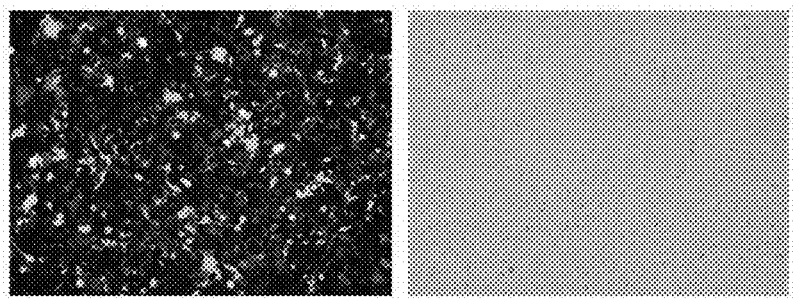
FIG. 4B is a verification result of rAAV prepared according to combination 2 in infecting HEK293 cells.
Figure 4C:
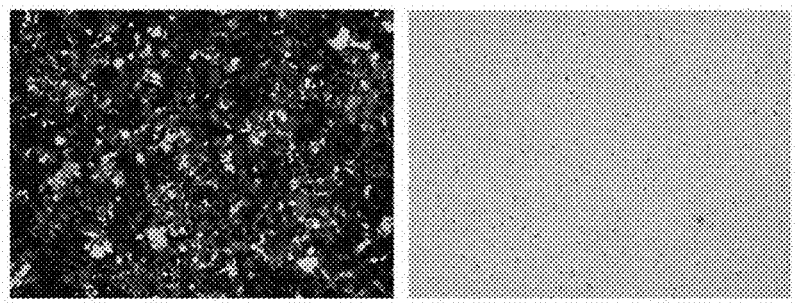
FIG. 4C is a verification result of rAAV prepared according to combination 3 in infecting HEK293 cells.

The HEK293 cells infected with rAAV prepared by using combinations 2 and in Example 1 were tested according to the above method. The experimental results show that the above rAAV infected HEK293 cells have significant GFP expression, as shown in FIGS. 4B and 4C. The above results demonstrate that the Bac-A system produces active rAAV.

Example 3: Purification and Titer Test of rAAV

Since the rAAV prepared via the three combinations in Example 1 is virtually indistinguishable, the rAAV prepared in Example 1 was taken as an example for the subsequent purification of the rAAV produced by the Bac-A system, detection of the activity, and the like.

About $1 \times 10^8$ Sf9 cells was collected after recombinant BEV infection. After adding 10 mL of lysis buffer (50 mM Tris-Cl, 150 mM NaCl, 2 mM MgCl$_2$, pH 8.0), the cell pellets were lysed by freeze-thaw using liquid nitrogen and a 37° C. water bath for three times, and then centrifuged at 5000 rpm for 5 min. The supernatant was collected, and nuclease Benzonase was added to the supernatant to a final concentration of 50 U/ml. The mixture was incubated in water bath at 37° C. for 60 min. After centrifugation at 5000 rpm for 10 min, the supernatant was collected. The supernatant was extracted with chloroform and the extracted supernatant was further purified by two-phase precipitation with a solution containing 13.2% (NH$_4$)$_2$SO$_4$ and 10% PEG8000 (J Virol Methods, 2007. 139 (1): 61-70, J Virol Methods, 2012. 179 (1): 276-80). The two-phase precipitated supernatant was dialyzed and desalted with a PBS solution and concentrated to a final volume of 1 mL by an Amicon ultra-4 (100 kD cutoff) dialysis column and stored at −80° C. after aseptic aliquots. The titer of rAAV was determined by fluorescence quantitative PCR, and the titer unit was expressed as virus genome (VG)/ml.

The rAAV yield of the purification process is shown in Table 1. The experimental results showed that the yield of rAAV in a single Sf9 packaging cell was up to $1.78 \times 10^5$ VG. After the purification, the recovery rate reached 32.9%.

TABLE 1 rAAV purification process yield analysis

| Purification step | Volume (mL) | rAAV concentration (VG/mL) | rAAV amount (VG) | rAAV yield (%) |
|---|---|---|---|---|
| Lysate treated supernatant | 20 | $8.91 \times 10^{11}$ | $1.78 \times 10^{13}$ | 100 |
| Chloroform treated supernatant | 20 | $7.54 \times 10^{11}$ | $1.51 \times 10^{13}$ | 84.8 |
| two-phase precipitated supernatant | 28 | $4.72 \times 10^{11}$ | $1.32 \times 10^{13}$ | 74.2 |
| Dialysis treated supernatant | 1 | $5.86 \times 10^{12}$ | $5.86 \times 10^{12}$ | 32.9 |

Example 4: Electron Microscopy and Integrity Assay of rAAV Particles

A drop of purified rAAV of 10 μL was adsorbed on a 200 mesh carbon-coated copper mesh for 5 min, and was then washed 4 times with ultrapure water, and then a drop of 1% uranyl acetate was added. The sample was dried in air for 5 min. Finally, the virus particles were observed by transmission electron microscopy.

Figure 5A:
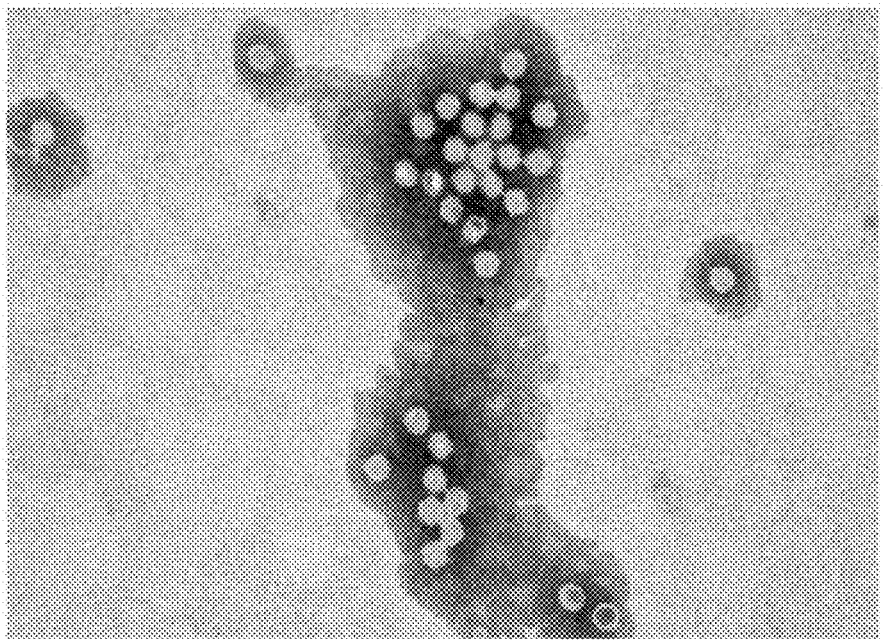
FIG. 5A is a TEM image after rAAV particles are negatively dyed.
Figure 5B:
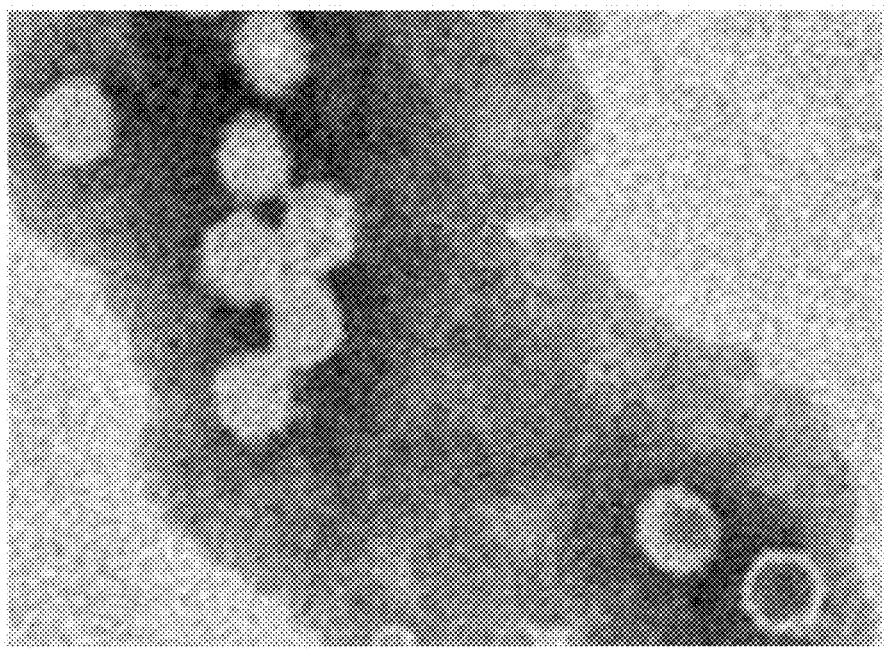
FIG. 5B is an enlarged view (2.5 times) of FIG. 5A.

The intact rAAV particles were hexagonal uniform particles and the defective rAAV particles that do not contain nucleic acid were dyed in middle part, as shown in FIGS. 5A and 5B. Electron micrographs showed that the ratio of intact rAAV particles was over 75%, and the results between different preparation batches were repeatable.

Figure 6A:
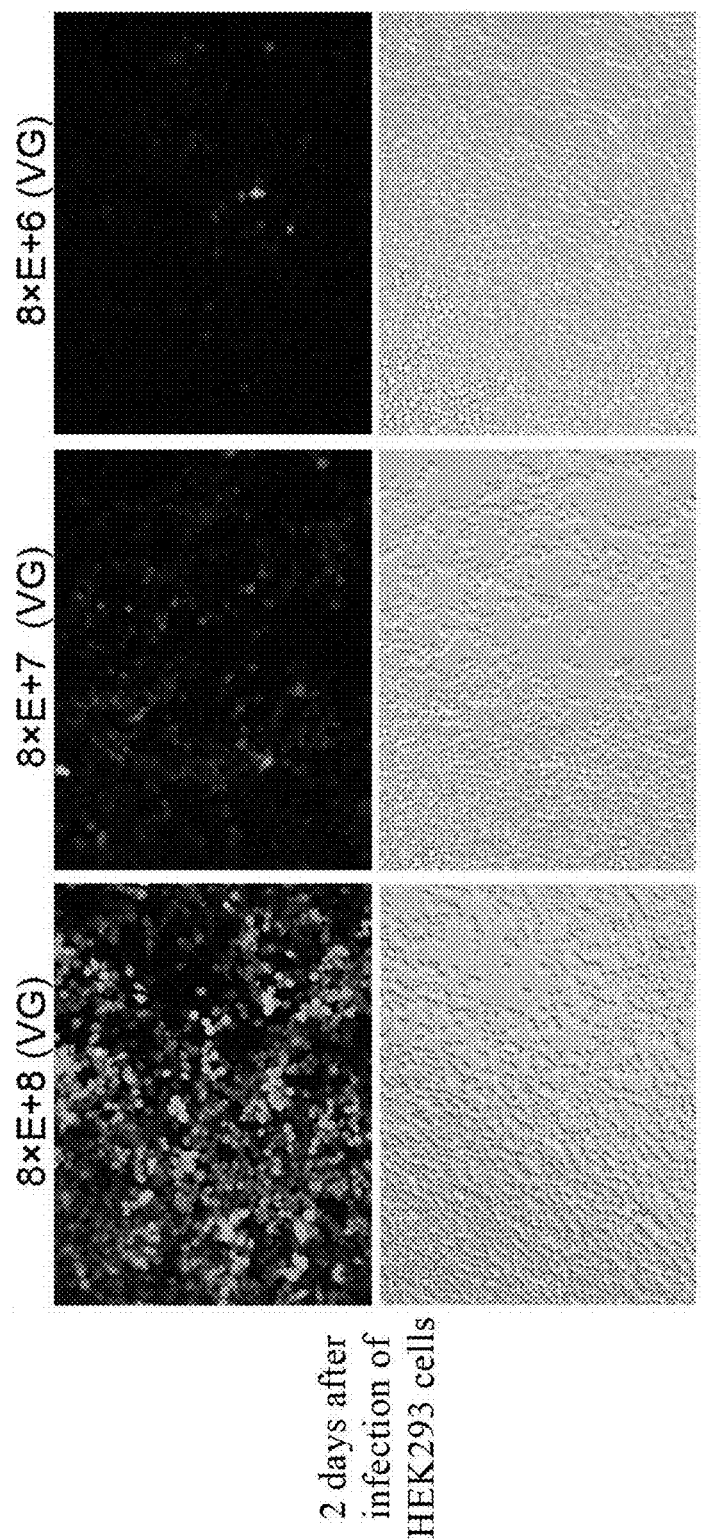
FIG. 6A is fluorescence microscopy images of HEK293 cells infected with purified rAAV.
Figure 6B:
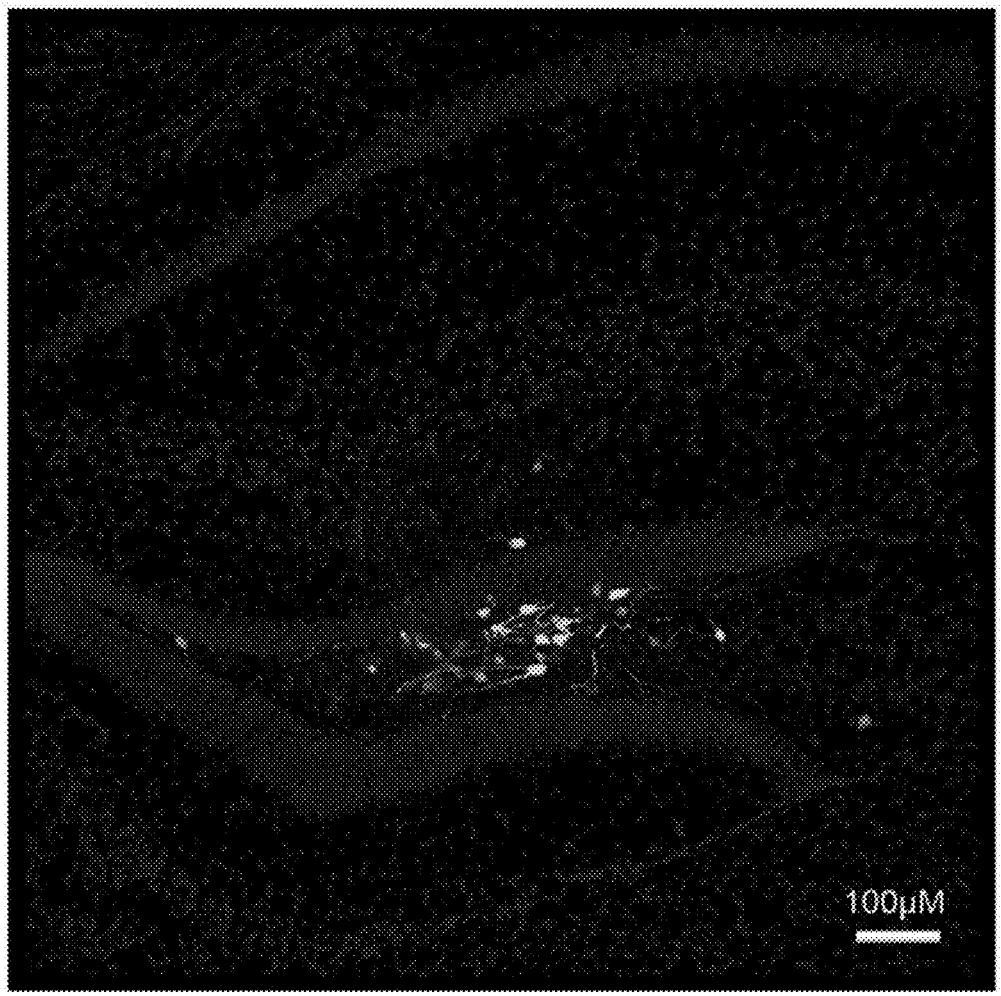
FIG. 6B is fluorescence microscopic images of the C57 mice hippocampal cortical neurons of mice infected with purified rAAV.
Figure 6C:
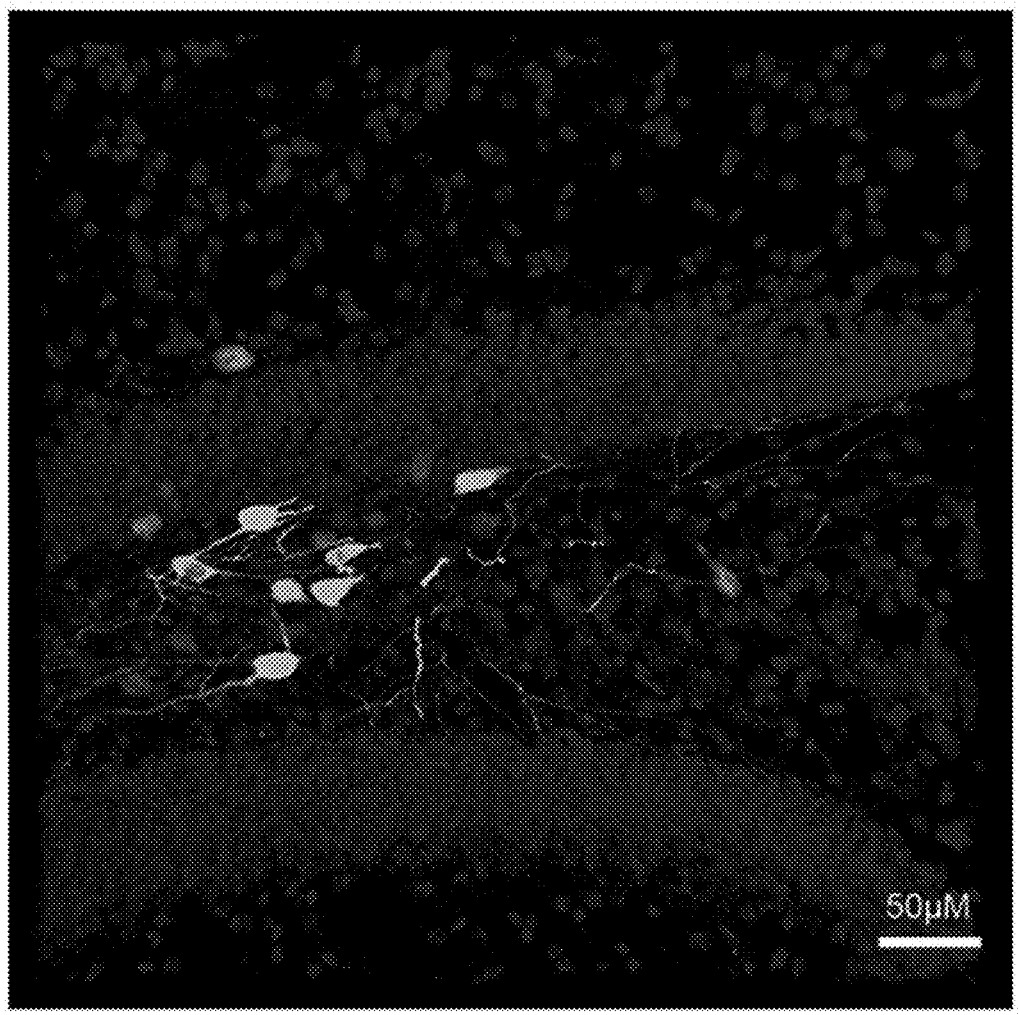
FIG. 6C is an enlarged view of FIG. 6B (2 times).

Example 5: Detection of rAAV Activity at Cell Level In Vitro and in Mouse Brain In Vivo HEK293 cells were seeded into 96-well plates at $1 \times 10^4$ cells/well and were infected with the purified rAAV of corresponding concentration gradient, and were detected by fluorescence microscopy GFP expression 48 h after infection, as shown in FIG. 6A. Purified rAAV was microinjected into hippocampus area of C57 mice brains. Three weeks after injection, the rat brain sections were taken to observe the rAAV infected mouse brain neurons under a fluorescence microscope. Green fluorescence was GFP expressed after rAAV infection and blue fluorescence was neuronal nuclei labeled with DAPI dye, as shown in FIG. 6B.

The above results show that the rAAV produced by the Bac-A system of the disclosure has high activities both in cultured cells and animal model.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A recombinant baculovirus, comprising: an adeno-associated virus (AAV) Rep gene, an AAV Cap gene, and a recombinant adeno-associated virus (rAAV) genome ITR-GOI (gene of interest) flanked by AAV inverted terminal repeats (ITR); wherein:
   the ITR-GOI comprises a 5' terminal nucleic acid fragment and a 3' terminal nucleic acid fragment; and
   the ITR-GOI is linked to an expression cassette of the Cap gene and an expression cassette of the Rep gene through the 5' terminal nucleic acid fragment and the 3' terminal nucleic acid fragment, respectively.

2. The recombinant baculovirus of claim 1, wherein the Rep gene has a codon-optimized sequence.

3. The recombinant baculovirus of claim 2, wherein the Rep gene has the sequence represented by SEQ ID NO: 1, SEQ ID NO: 2, or SEQ ID NO: 3.

4. The recombinant baculovirus of claim 1, wherein the Cap gene has a codon-optimized sequence.

5. The recombinant baculovirus of claim 4, wherein the Cap gene has the sequence represented by SEQ ID NO: 4, SEQ ID NO: 5, or SEQ ID NO: 6.

6. The recombinant baculovirus of claim 1, wherein each of two ends of the rAAV genome ITR-GOI comprises an inverted terminal repeat (ITR) of the adeno-associated virus genome; and the gene of interest (GOI) is disposed between the two ends of the ITR-GOI.

7. The recombinant baculovirus of claim 1, wherein the inverted terminal repeat (ITR) has a sequence represented by SEQ ID NO: 7.

8. The recombinant baculovirus of claim 1, wherein the 5' terminal nucleic acid fragment and the 3' terminal nucleic acid fragment have a length of 80-140 bp.

9. The recombinant baculovirus of claim 1, wherein the 5' terminal nucleic acid fragment and the 3' terminal nucleic acid fragment have a sequence represented by SEQ ID NO: 8 or SEQ ID NO: 9.

10. The recombinant baculovirus of claim 1, wherein the adeno-associated virus is adeno-associated virus serotype 2.

11. A method for preparing a recombinant adeno-associated vims vector, the method comprising:
   (a) constructing a baculovirus by integrating a target gene into a genome of the recombinant baculovirus of claim 1;
   (b) infecting an isolated host cell with the baculovirus of (a) to produce a recombinant adeno-associated virus; and
   (c) purifying the recombinant adeno-associated virus of (b).

12. The method of claim 11, wherein in (a), a shuttle vector based on a baculovirus expression system is used.

* * * * *

SEQUENCE LISTING

```
<160> NUMBER OF SEQ ID NOS: 12

<210> SEQ ID NO 1
<211> LENGTH: 1866
<212> TYPE: DNA
<213> ORGANISM: Artificial Sequence
<220> FEATURE:
<223> OTHER INFORMATION: Fully synthetic

<400> SEQUENCE: 1
ctggcggggt tctacgaaat tgtcattaag gtcccaagcg acctggacgg gcatctgccc      60
ggcatttccg acagcttcgt gaactgggtg gccgagcagg agtgggagtt accgccagat     120
tctgacttag atctgaatct aattgagcag gcgcccctga ctgtggccga gaagctgcag     180
cgcgactttc taacggagtg gcgccgtgtg agtaaggccc cggaggccct tttctttgtg     240
caatttgaca agggagagag ctatttccac ttacacgtgc tagtggaaac caccggggtg     300
aaatccttag ttttgggacg tttcctgagt cagattcgcg aaaaactgat tcagaggatt     360
taccgcggga tcgagccgac tttgccgaac tggttcgcgg tcacaaagac cagaaacggt     420
gccggaggcg ggaacaaggt ggtcgacgag tgctacatcc ccaattattt gctcccgaaa     480
acccagcctg agctccagtg ggcctggact aatttcgaac agtacttaag cgcctgtttg     540
aatctcacgg agcgtaaacg gttggtggcg cagcatctga cgcacgtgtc gcagacgcag     600
gatcagaaca aagagaatca gaatcccaat tctgacgcgc cggtgatcag atcaaaaacg     660
tcagccaggt acatggagct agtcgggtgg ctcgtggata agggggattac ctcggagaag     720 cactggatcc aggaggacca ggcttcatac atctccttca atgcggcctc caagtcgcgg     780
tcccaaatca aggctgcgtt ggacaatgcg ggtaagatta tgagcctgac taaaaccgcc     840
cccgactatc tggtgggcca gcagcccgtg gaagacattt ccagcaatcg gatttataaa     900 atttttggagc taaacgggta cgatccccaa tatgctgctt cagtctttct gggatgggcc     960
acgaaaaagt tcggcaagag gaacaccatc tggctgtttg gccctgcaac taccgggaag    1020
accaacatcg cagaggcaat agcccacact gtgcccttct acgggtgcgt aaactggacg    1080
aatgagaact tccccttcaa cgactgtgtc gacaaaatgg tgatctggtg ggaagagggg    1140
aagatgaccg ccaaggtcgt ggagtcggcc aaagcgattc taggaggaag caaggtgcgc    1200
gtggaccaga agtgcaagtc gtcggcccag atagatccga ctcccgtgat cgtcacctcg    1260
aacacgaaca tgtgcgccgt gattgacggc aactcaacga cgttcgaaca ccagcagccg    1320
ttgcaggacc gtatgttcaa atttgaactc acccgccgtc tcgatcatga cttcgggaag    1380
gtcaccaagc aggaagtcaa ggacttcttc cggtgggcaa aggatcacgt ggttgacgtg    1440
gagcacgaat tctacgtcaa aaagggtgga gccaagaaga gaccagcccc cagtgacgca    1500
gatataagcg agccaaagcg ggtgcgagag tcagttgcgc agccatcgac gtcagacgcg    1560
aaagcttcga taaactacgc ggacaggtac caaaacaaat gttctcgaca cgtcggcatg    1620
aatctaatgc tgttcccttg cagacaatgc gagaggatga atcaaaattc gaatatctgt    1680
```

-continued

| | |
|---|---|
| ttcactcacg acagaaaga ctgtttggag tgcttgcccg tgtcagagtc tcaacctgtt | 1740 |
| tctgtcgtca agaaggcgta tcagaagctg tgctacattc atcatatcat gggcaaggtg | 1800 |
| ccggacgctt gcactgcgtg cgacctggtc aatgtagatt tggacgactg catcttcgaa | 1860 |
| caataa | 1866 |

<210> SEQ ID NO 2
<211> LENGTH: 1866
<212> TYPE: DNA
<213> ORGANISM: Artificial Sequence
<220> FEATURE:
<223> OTHER INFORMATION: Fully synthetic

<400> SEQUENCE: 2

| | |
|---|---|
| ctggcggggt tctacgaaat tgtcattaag gtcccaagcg acctggacgg gcatctgccc | 60 |
| ggcatttctg acagcttcgt gaactgggtg gccgagcagg agtgggagtt gccgccagat | 120 |
| tctgacttag atctgaatct gattgagcag gcgcccctga ctgtggccga gaagctgcag | 180 |
| cgcgactttc taacggagtg gcgccgtgtg agtaaggccc cggaggccct tttctttgtg | 240 |
| caatttgaca agggagagag ctacttccac ttacacgtgc tagtggaaac caccggggtg | 300 |
| aaaatccttag ttttgggacg tttcctgagt cagattcgcg aaaaactgat tcagaggatt | 360 |
| taccgcggga tcgagccgac tttgccgaac tggttcgcgg tcacaaagac cagaaacggt | 420 |
| gccggaggcg ggaacaaggt ggtggacgag tgctacatcc ccaattactt gctccccaaa | 480 |
| acccagcctg agctccagtg ggcgtggact aatttagaac agtatttaag cgcctgtttg | 540 |
| aatctcacgg agcgtaaacg gttggtggcg cagcatctga cgcacgtgtc gcagacgcag | 600 |
| gagcagaaca aagagaatca gaatcccaat tctgacgcgc cggtgatcag atcaaaaact | 660 |
| tcagccaggt acatggagct agtcgggtgg ctcgtggata aggggattac ctcggagaag | 720 |
| cactggatcc aggaggacca ggcttcatac atctccttca atgcggcctc caagtcgcgg | 780 |
| tcccaaatca aggctgcgtt ggacaatgcg ggtaagatta tgagcctgac taaaaccgcc | 840 |
| cccgactatc tggtgggcca gcagcccgtg aagacatttt ccagcaatcg gatttataaa | 900 |
| attttggagc taaacggcta cgacccacaa tatgcggctt ccgtctttct gggatgggcc | 960 |
| acgaaaaagt tcggcaagag gaacaccatc tggctgtttg ggcctgcgac tacagggaaa | 1020 |
| accaatatcg cggaggccat agcccacact gtgcccttct acgggtgcgt aaactgacc | 1080 |
| aatgagaact ttcccttcaa cgattgtgta gacaaaatgg tgatctggtg ggaggagggg | 1140 |
| aagatgaccg ccaaggtcgt ggagtcggcc aaagccattc tcggaggaag caaggtacgc | 1200 |
| gtggaccaga aatgcaagtc ctcggcccag atagacccga ctcccgtgat cgtcacctcc | 1260 |
| aacaccaaca tgtgtgccgt aattgacggc aactcaacga ccttcgaaca ccagcagccg | 1320 |
| ttgcaagacc ggatgttcaa gtttgaactc actcgccgtc tggatcatga ctttgggaag | 1380 |
| gtcaccaagc aggaagtcaa agacttttc cggtgggcaa agatcacgt ggtcgaggtg | 1440 |
| gagcatgaat tctacgtcaa aaagggtgga gccaagaaaa gaccccgctcc cagtgatgca | 1500 |
| gatataagcg agcccaaacg ggtgcgcgag tcagttgcgc agccatcgac gtcagacgcg | 1560 |
| gaagcttcga tcaactacgc agacaggtac cagaacaagt gttctcgtca tgtgggcatg | 1620 |
| aatctgatgc tgtttccctg cagacaatgc gagagaatga atcagaattc aaatatctgt | 1680 |
| ttcactcacg ggcagaagga ctgtttagag tgctttcccg tgtcagaatc tcaacccgtt | 1740 |
| tctgtcgtca aaaaggcgta tcagaaactg tgctatattc atcatataat gggcaaggtg | 1800 |
| ccagacgctt gcactgcctg cgatctggtc aatgtggatt tggacgactg catcttggaa | 1860 | caataa 1866

<210> SEQ ID NO 3
<211> LENGTH: 1866
<212> TYPE: DNA
<213> ORGANISM: Artificial Sequence
<220> FEATURE:
<223> OTHER INFORMATION: Fully synthetic

<400> SEQUENCE: 3

```
ctggcggggt tctacgaaat tgtcattaag gtcccaagcg acctggacgg gcatctgccc      60
ggcatttctg acagcttcgt gaactgggtg gccgagcagg agtgggagtt gccgccagat     120
tctgacttag atctgaacct gattgagcag gcacccctga ccgtggccga gaagctgcag     180
cgcgactttc tgacggagtg gcgccgtgtg agtaaggccc cggaggccct tttctttgtg     240
caatttgaca agggagagag ctatttccac ttacacgtgc tagtggaaac caccggggtg     300
aaatccttag ttttgggacg tttcctgagt cagattcgcg aaaaactgat tcagaggatt     360
taccgcggga tcgagccgac tttgccgaac tggttcgcgg tcacaaagac cagaaacggt     420
gccgaggcg gaaacaaggt ggtcgacgag tgctacatcc ccaattattt gctcccgaaa      480
acccagcctg agctccagtg ggcctggact aatttcgaac agtacttaag cgcctgtttg     540
aatctcacgg agcgtaaacg gttggtggcg cagcatctga cgcacgtgtc gcagacgcag     600
gatcagaaca agagaatca aaatcccaat tctgacgcgc cggtgatcag atcaaaaacg      660
tcagccaggt acatggagct ggtcggctgg ctcgtggaca aggggattac ctcggagaag     720
cagtggatcc aggaggacca ggcctcatac atctccttca atgcggcctc caactcgcgg     780
tcccaaatca aggctgcctt ggacaatgcg ggaaagatta tgagcctgac taagaccgcc     840
cccgactacc tggtgggcca gcagcccgtg gaggacattt ccagcaatcg gatttataaa     900
attttggaac taaacggcta cgacccacaa tatgcggctt ccgtctttct gggatgggcc     960
acgaaaaagt tcggcaagag gaacaccatc tggctgtttg ggcctgcgac tacagggaaa    1020
accaatatcg cggaggccat agcccacact gtgcccttct acgggtgcgt aaactggacc    1080
aatgagaact ttcccttcaa cgattgtgta gacaaaatgg tgatctggtg ggaggaggg    1140
aagatgaccg ccaaggtcgt ggagtcggcc aaagccattc tcggaggaag caaggtacgc    1200
gtggaccaga atgcaagtc ctcggcccag atagacccga ctcccgtgat cgtcacctcc     1260
aacaccaaca tgtgtgccgt aattgacggc aactcaacga ccttcgaaca ccagcagccg    1320
ttgcaagacc ggatgttcaa gtttgaactc actcgccgtc tggatcatga ctttgggaag    1380
gtcaccaagc aggaagtcaa agacttttc cggtgggcaa agatcacgt ggtcgaggtg      1440
gagcatgaat tctacgtcaa aaagggtgga gccaagaaaa gacccgctcc cagtgatgca    1500
gatataagcg agcccaaacg ggtgcgcgag tcagttgcgc agccatcgac gtcagacgcg    1560
gaagcttcga tcaattacgc agacaggtac cagaacaagt gttctcgtca tgtgggcatg    1620
aatctgatgc tgtttccctg cagacaatgc gagagaatga atcagaattc aaatatctgt    1680
ttcactcacg gcagaagga ctgtttagag tgctttcccg tgtcagaatc tcaacccgtt     1740
tctgtcgtca aaaggcgta tcagaaactg tgctatattc atcatataat gggcaaggtg    1800
ccagacgcgt gcactgcttg cgatctggtc aatgtggatt tggacgactg catcttggaa    1860
caataa                                                              1866
```

<210> SEQ ID NO 4

<211> LENGTH: 2208
<212> TYPE: DNA
<213> ORGANISM: Artificial Sequence
<220> FEATURE:
<223> OTHER INFORMATION: Fully synthetic

<400> SEQUENCE: 4

| | |
|---|---|
| acggctgccg acggttacct acccgactgg ctcgaagaca ctctgtctga aggtataaga | 60 |
| cagtggtgga agctcaagcc tggcccaccg ccaccaaagc ctgcagagcg cataaggac | 120 |
| gacagcagag gtcttgtgct acctgggtac aagtacctcg gacccttcaa cgggctcgac | 180 |
| aagggcgagc cggtcaacga ggcagacgcc gcggccctcg agcacgacaa agcgtacgac | 240 |
| cggcagctcg acagcggaga caatccgtac ctcaaataca accacgccga cgcggagttt | 300 |
| caggagcgcc ttaaagaaga tacgtctttt ggggcaacc tcggacgagc agtcttccaa | 360 |
| gcgaagaaga gggttcttga acctctgggc ctggtcgagg aacctgttaa gacggctccg | 420 |
| ggaaaaaga ggccggtaga cactcccct gtggagccag actcctcctc gggaacagga | 480 |
| aaggcgggtc agcagcctgc aagaaaaaga ttgaattttg gtcagactgg agacgcagat | 540 |
| tcagtgcctg accccagcc tctcggacag ccgccagcag caccctctgg tctgggaact | 600 |
| aatacgatgg ctacaggcag tggcgcacca atggcagaca taacgaggg cgccgacgga | 660 |
| gtgggtaatt catcgggaaa ttggcattgc gattccacgt ggatgggaga cagagtcatc | 720 |
| accaccagca cccgaacctg ggccctgccc acctacaaca accacctcta caagcaaatt | 780 |
| tcgagccaat caggagcctc gaacgataat cactacttcg gctacagcac cccttggggg | 840 |
| tattttgatt tcaacaggtt ccactgccac ttttcaccac gtgactggca gagactcatc | 900 |
| aataacaact ggggattccg acccaagaga ctcaacttca agctctttaa cattcaagtc | 960 |
| aaggaggtca cgcagaatga cggtacgacg acgattgcca ataatcttac cagcacggtt | 1020 |
| caggtgttta ctgactcgga gtaccagctc ccgtacgtcc tcgactcggc gcatcaagga | 1080 |
| tgcctcccgc cgtttccagc agacgtattc atggtgccac agtatggata cctcaccctg | 1140 |
| aacaacggga gtcaggcagt gggacgctct tcatttact gcctggagta cttgccttct | 1200 |
| cagatgctgc gtaccggaaa caactttacc ttcagctaca cttttgagga cgtccctttc | 1260 |
| cacagcagtt acgctcacag ccagagtctg gaccgtctca tgaatccact catcgatcag | 1320 |
| tacctgtatt acttgagcag aacaaacact ccaagtggaa caaccacgca gtcaaggctt | 1380 |
| cagttctctc aggcaggagc gagtgacatt cgggaccagt ctaggaactg gcttcctgga | 1440 |
| ccctgttacc gccagcagcg agtttcaaaa acatctgcgg ataacaacaa cagtgagtac | 1500 |
| tcttggactg gagctaccaa gtaccacctc aatggcagag actctctggt gaatccgggc | 1560 |
| ccggctatgg caagtcacaa ggacgatgaa gaaaagtttt tcctcaaag cggagttctc | 1620 |
| atctttggga agcaaggctc agagaaaaca aatgtagaca tcgaaaaggt catgattaca | 1680 |
| gacgaagagg aaatcagaac aacaaatccc gtggctacgg agcagtatgg ttctgtatct | 1740 |
| accaacctcc agagaggcaa cagacaagcg gctacagcag atgtcaacac acaaggcgtt | 1800 |
| cttccaggca tggtttggca cgacagagat gtgtaccttc aggggcccat ctgggcaaaa | 1860 |
| attccgcaca cggacggaca ttttcacccc tctccactca tgggaggatt cggacttaaa | 1920 |
| caccctcctc cacagattct catcaagaac accccggtac ctgcaaatcc ttcgacgacc | 1980 |
| ttcagtgcgg caaagtttgc ttccttcatc acgcagtact caacgggaca ggtcagcgtg | 2040 |
| gagatcgagt gggagctgca aaaggagaac agcaagcgct ggaatcccga aattcagtac | 2100 |
| acctccaact ataacaagtc tgtcaatgtg gacttcactg tggacactaa tggcgtgtat | 2160 |

<210> SEQ ID NO 5
<211> LENGTH: 2208
<212> TYPE: DNA
<213> ORGANISM: Artificial Sequence
<220> FEATURE:
<223> OTHER INFORMATION: Fully synthetic

<400> SEQUENCE: 5

```
tcagagccac gccccatagg caccagatat ctgactcgca atctgtaa              2208
```

```
acggctgccg acggttacct acccgactgg ctcgaagaca ctctgtctga aggtataaga   60
cagtggtgga agctcaagcc tggcccaccg ccaccaaagc ctgcagagcg cataaggac   120
gacagcagag gtcttgtgct acctgggtac aaatacctcg gacccttcaa cgggctcgac  180
aagggcgagc cggtcaacga ggcagacgcc gcggccctcg agcacgacaa agcgtacgac  240
cggcagctag acagcggaga caatccgtac ctcaaataca accacgccga cgcggagttt  300
caggagcgcc ttaaagaaga tacgtctttt gggggcaacc tcggacgagc agtcttccaa  360
gcgaagaaga gggttcttga gcctctgggc ctggttgagg aacctgttaa gacggctccg  420
ggaaaaaaga ggccggtaga gcactctcct gtggagccgg actcctcttc gggaaccgga  480
aaggcgggcc agcagcctgc aagaaaaaga ttgaattttg gtcagactgg agacgcagac  540
tcagtacctg acccacagcc tctgggacag ccaccagcag cccctctggg tctgggaact  600
aatacgatgg ctacaggcag tggcgcacca atggcagaca taacgagggg cgccgacgga  660
gtgggtaatt cctcgggaaa ctggcattgt gattccacat ggatgggcga cagagtcatc  720
accaccagca cccgaacctg ggccctgccc acctacaaca accacctcta caaacaaatt  780
tcaagccaat caggtgcctc gaatgacaat cactactttg ctacagcac cccttggggg  840
tattttgact tcaacaggtt ccactgccac ttctcaccgc gtgactggca agactcatc   900
aacaacaact ggggattccg acccaagaga ctcaacttca gctctttaa cattcaagtc  960
aaagaggtca cacagaatga tggtacgacg acgattgcca ataaccttac cagcacggtt  1020
caggtgtttt ctgactcgga gtaccagctc ccgtacgtcc tcggctcggc gcgtcaagga  1080
tgtctcccgc cgttcccagc agacgtcttc atggtgccac agtatggata cctcaccctg  1140
aacaacggga gtcaggcagt aggacgctct tcattctact gtctggagta ctttccttct  1200
cagatgctgc gtaccggaaa caactttacc ttcagctaca cttttgagga cgttcctttc  1260
cacagcagct acgctcacag ccaaagtcta gaccgtctca tgaatcctct catcgaccag  1320
tacctgtatt acttgagcag aacaaacact ccaagtggaa ccaccacgca gtcaagactt  1380
cagttctctc aggccggagc gagtgacatt cgggaccagt ctaggaactg cttcctgga   1440
ccctgttacc gccagcagcg agtatcaaag acatctgcgg ataataacaa cagtgagtac  1500
tcgtggactg gagctaccaa gtaccacctc aatggcagag actctctggt gaatccgggc  1560
ccggccatgg caagccataa ggacgatgaa gagaaattct ttcctcagag cggggttctc  1620
atctttggga agcaaggctc agagaaaaca aatgtggaca ttgaaaaggt catgatcaca  1680
gacgaagaag aaatcaggac aaccaatccc gtggctacgg agcagtatgg ttctgtatct  1740
accaacctcc agagaggcaa cagacaagca gctaccgcag atgtcaatac acaaggcgtc  1800
cttccaggta tggtctggca ggacagagat gtgtaccttc aggggccat ctgggcaaag  1860
attccacaca cggacggaca tttccaccca tctccactca tgggtggatt tggacttaaa  1920
catcctcctc cacagattct catcaagaac accccggtac ctgcgaatcc ttcgaccacc  1980
```

```
ttcagtgcag caaagttcgc ttccttcatc acacagtact ccacgggaca ggtcagcgtg    2040
gagatcgagt gggagctgca gaaggagaac agcaaacgct ggaaccccga gattcagtac    2100
acttccaact acaacaagtc tgttaatgtg gactttactg tggacactaa tggagtgtat    2160
tcagaacctc gcccaattgg cacgagatac ctcactcgta atctgtaa                 2208

<210> SEQ ID NO 6
<211> LENGTH: 2208
<212> TYPE: DNA
<213> ORGANISM: Artificial Sequence
<220> FEATURE:
<223> OTHER INFORMATION: Fully synthetic

<400> SEQUENCE: 6
acggctgccg acggttacct acccgactgg ctcgaagaca ctctgtctga aggtataaga      60
cagtggtgga agctcaagcc tggcccaccg ccaccaaagc ctgcagagcg gcataaggac     120
gacagcagag gtcttgtgct acctgggtac aagtacctcg gacccttcaa cgggctcgac     180
aagggcgagc cggtcaacga ggcagacgcc gcggccctcg agcacgacaa agcgtacgac     240
cggcagctcg acagcggaga caatccgtac ctcaaataca accacgccga cgcggagttt     300
caggagcgcc ttaaagaaga tacgtctttt ggggcaacc tcggacgagc agtcttccaa     360
gcgaagaaga gggttcttga acctctgggc ctggttgagg aacctgttaa gacggctccg     420
ggaaaaaaga ggccggtaga gcactctcct gtggagccag actcctcctc gggaaccgga     480
aaggcgggcc agcagcctgc aagaaaaaga ttgaattttg gtcagactgg agacgcagac     540
tcagtacctg acccacagcc tctgggacag ccaccagcag cccctctgg tctgggaact     600 aatacgatgg ctacaggcag tggcgcacca atggcagaca taacgaggg cgccgacgga     660 gtgggtaatt cctcgggaaa ctggcattgt gattccacat ggatgggcga cagagtcatc     720
accaccagca cccgaacctg ggccctgccc acctacaaca accacctcta caaacaaatt     780
tccagccaat caggtgcctc gaacgacaat cactactttg ctacagcac ccttgggg      840 tattttgact tcaacagatt ccactgccac ttctcaccgc gtgactggca aagactcatc     900
aacaacaact ggggattccg acccaagaga ctcaacttca gctctttaa cattcaagtc     960 aaagaggtca cacagaatga tggtacgacg acgattgcca ataaccttac cagcacggtt    1020
caggtgttta ctgactcgga gtaccagctc ccgtacgtcc tcggctaggc gcatcaagga    1080
tgcctcccgc cattcccagc agacgtcttc atggtgccac agtatggata cctcaccctg    1140
aacaacggga gtcaggcagt aggacgctct tcattctact gcctggagta ctttccttct    1200
cagatgctgc gtaccggaaa caactttacc ttcagctaca cttttgagga cgttcctttc    1260
cacagcagct acgctcacag ccagagtcta gaccgtctca tgaatcctct catcgaccag    1320
tacctgtatt acttgagcag aacaaacact ccaagtggaa ccaccacgca gtcaagactt    1380
cagttctctc aggccggagc gagtgacatt cgggaccagt ctaggaactg gcttcctgga    1440 cctgttacc gccagcagcg agtatcaag acatctgcgg ataataacaa cagtgaatac    1500
tcgtggacag gagctaccaa gtaccacctc aatggcagag actctctggt gaatccgggc    1560
ccggccatgg caagccacaa ggacgatgaa gagaagtttt tccctcagag cggggttctc    1620
atctttggga agcaaggctc agagaaaaca aatgtggaca ttgaaaaggt catgattacg    1680
gacgaagagg agatcaggac aaccaatccc gtggctacgg agcagtatgg ttctgtatct    1740
accaacctcc agagaggcaa cagacaagca gctaccgcag atgtcaacac acaaggcgtt    1800
cttccaggca tggtttggca cgacagagat gtgtaccttc aggggcccat ctgggcaaaa    1860
```

```
attccgcaca cggacggaca tttcacccc tctccactca tgggaggatt cggacttaaa    1920 cacctcctc cacagattct catcaagaac acccggtac ctgcaaatcc ttcgacgacc    1980
ttcagtgcgg caaagtttgc ttccttcatc acgcagtact caacgggaca ggtcagcgtg    2040
gagatcgagt gggagctgca gaaggagaac agcaagcgct ggaatcccga aattcagtac    2100
acctccaact ataacaagtc tgtcaatgtg gacttcactg tggacactaa tggcgtgtat    2160
tcagagccac gccccatagg caccagatat ctgactcgca atctgtaa                2208
```

<210> SEQ ID NO 7
<211> LENGTH: 141
<212> TYPE: DNA
<213> ORGANISM: Artificial Sequence
<220> FEATURE:
<223> OTHER INFORMATION: Fully synthetic

<400> SEQUENCE: 7

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggttcc t                                              141
```

<210> SEQ ID NO 8
<211> LENGTH: 140
<212> TYPE: DNA
<213> ORGANISM: Artificial Sequence
<220> FEATURE:
<223> OTHER INFORMATION: Fully synthetic

<400> SEQUENCE: 8

```
tacagctcga tatactgcgg aagtctgatc tgagcatcga ttattgtcta gctcgtcaga    60
ggcgctgaac ctatcgataa actccagaaa tgcagcctat taaccgttgc tagcctattg   120
cacgccttca gctgtcatgt                                               140
```

<210> SEQ ID NO 9
<211> LENGTH: 81
<212> TYPE: DNA
<213> ORGANISM: Artificial Sequence
<220> FEATURE:
<223> OTHER INFORMATION: Fully synthetic

<400> SEQUENCE: 9

```
gcggctcgat cgcgtattat ctagttaccg atctgaccgg aatatcacag cgcactcgtc    60
tcagcatcga tactgactac t                                              81
```

<210> SEQ ID NO 10
<211> LENGTH: 122
<212> TYPE: DNA
<213> ORGANISM: Artificial Sequence
<220> FEATURE:
<223> OTHER INFORMATION: Fully synthetic

<400> SEQUENCE: 10

```
atacggacct taattcaac ccaacacaat atattatagt taaataagaa ttattatcaa     60
atcatttgta tattaattaa aatactatac tgtaaattac atttattta caatcactcg    120 ac                                                                  122
```

<210> SEQ ID NO 11
<211> LENGTH: 128
<212> TYPE: DNA

```
<213> ORGANISM: Artificial Sequence
<220> FEATURE:
<223> OTHER INFORMATION: Fully synthetic

<400> SEQUENCE: 11
atcatggaga taattaaaat gataaccatc tcgcaaataa ataagtattt tactgttttc      60
gtaacagttt tgtaataaaa aaacctataa atattccgga ttattcatac cgtcccacca    120
tcgggcgc                                                             128

<210> SEQ ID NO 12
<211> LENGTH: 18
<212> TYPE: DNA
<213> ORGANISM: Artificial Sequence
<220> FEATURE:
<223> OTHER INFORMATION: Fully synthetic

<400> SEQUENCE: 12
actccggaat attaatag                                                   18
```